US00PP34837P2

(12) United States Plant Patent
Glawe et al.

(10) Patent No.: US PP34,837 P2
(45) Date of Patent: Dec. 13, 2022

(54) ***PELARGONIUM* PLANTED NAMED 'KLEPZ21596'**

(50) Latin Name: ***Pelargonium zonale* (L.) L'Hér. ex Aiton**
Varietal Denomination: KLEPZ21596

(71) Applicant: KLEMM + SOHN GMBH & CO. KG, Stuttgart (DE)

(72) Inventors: Martin Glawe, Stuttgart (DE); Nina Neu, Weissach im Tal (DE)

(73) Assignee: KLEMM+SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 17/732,014

(22) Filed: Apr. 28, 2022

(51) Int. Cl.
*A01H 5/02* (2018.01)
*A01H 6/42* (2018.01)

(52) U.S. Cl.
USPC ..... Plt./329

(58) Field of Classification Search
USPC ..... Plt./329
CPC ..... A01H 5/02; A01H 6/42; A01H 6/425
See application file for complete search history.

(56) References Cited

U.S. PATENT DOCUMENTS

PP13,743 P2 * 4/2003 Klemm ..... A01H 6/42 Plt./325

OTHER PUBLICATIONS

Ball Seed Moonlight Raspberry Blush 23 Zonal Geranium, retrieved on Jun. 1, 2022 at https://www.ballseed.com/PlantInfo/?phid=028902331037625, one page. (Year: 2022).*
Cherry Valley Gardens Geranium Moonlight Raspberry Blush, retrieved on Jun. 6, 2022 at https://www.cherryvalleygardens.com/shop/Geranium-Moonlight-Raspberry-Blush-p186731219, one page. (Year: 2022).*

* cited by examiner

*Primary Examiner* — June Hwu
(74) *Attorney, Agent, or Firm* — Weatherly IP Solutions, LLC; James M. Weatherly

(57) ABSTRACT

A new *Pelargonium* plant particularly distinguished by purple-pink flower color with a dark red spot and light pink center, is disclosed.

1 Drawing Sheet

Genus and species: *Pelargonium zonale* (L.) L'Her. ex Aiton.
Variety denomination: 'KLEPZ21596'.

BACKGROUND OF THE NEW PLANT

The present invention comprises a new and distinct variety of *Pelargonium*, botanically known as *Pelargonium zonale* (L.) L'Her. ex Aiton and hereinafter referred to by the variety name 'KLEPZ21596'. 'KLEPZ21596' originated from a hand-pollination in July 2015 in Nairobi, Kenya between the female *Pelargonium* variety Endisch Hot Spot Kiss (patent status unknown) and the male *Pelargonium* variety 'KLEPZ07202' (U.S. Plant Pat. No. 19,960).

Seeds from the hand-pollination were obtained. The seeds were sown and plants were grown for evaluation. A single plant was selected in June 2017 and subsequently named 'KLEPZ21596'. In July 2017 'KLEPZ21596' was first vegetatively propagated by vegetative stem cuttings in Stuttgart, Germany. 'KLEPZ21596' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Purple-pink flower color with a dark red spot and light pink center.

DESCRIPTION OF THE PHOTOGRAPH

This new *Pelargonium* plant is illustrated by the accompanying photograph which shows an overall view of the plant in a pot. The photograph is of an approximately 13-week-old plant grown indoors in Stuttgart, Germany, in January 2021. The colors shown are as true as can be reasonably obtained by conventional photographic procedures.

DESCRIPTION OF THE NEW VARIETY

The following detailed descriptions set forth the distinctive characteristics of 'KLEPZ21596'. The data which define these characteristics were collected from asexual reproductions carried out in Stuttgart, Germany. Data was collected on 9-week-old plants in Stuttgart, Germany under greenhouse conditions in April 2022. Color references are to The R.H.S. Colour Chart of The Royal Horticultural Society of London (R.H.S.), 5$^{th}$ edition (2007).

Classification:
*Family.*—Geraniaceae.
*Botanical.—Pelargonium zonale* (L.) L'Her. ex Aiton.
*Common.—Pelargonium.*
*Designation.*—'KLEPZ21596'.

Parentage:
*Female parent*.—Endisch Hot Spot Kiss (patent status unknown).
*Male parent*.—'KLEPZ07202' (U.S. Plant Pat. No. 19,960).

Plant:
*Form*.—Bushy.
*Habit*.—Mounding.
*Height* (*from top of soil*).—14.0 cm.
*Width* (*horizontal plant diameter*).—18.5 cm.
*Natural flowering season*.—March to October.
*Propagation type*.—Vegetative by stem cuttings.
*Time to produce a finished flowering plant*.—12 weeks.
*Time to initiate and develop roots*.—4 weeks.
*Root description*.—Fine, dense, RHS N155A (White).

Stems:
*Quantity of stems per plant*.—3.
*Color*.—RHS 146B.
*Surface texture*.—Pubescent, sparse.
*Stem form*.—Round.
*Diameter*.—0.5 cm.
*Length*.—4.0 cm to 7.0 cm.
*Internode length*.—1.5 cm.
*Anthocyanin*.—Absent.

Leaves:
*Arrangement*.—Alternate.
*Shape*.—Reniform.
*Apex*.—Round.
*Base*.—Open.
*Margin*.—Crenate.
*Depth of sinus*.—1.8 cm.
*Surface texture*.—Upper surface: Sparsely pubescent. Lower surface: Sparsely pubescent.
*Length*.—4.0 cm.
*Width*.—5.5 cm.
*Color*.—Upper surface: RHS N137A. Lower surface: RHS 137C.
*Zonation*.—Very weak.
*Zonation color*.—RHS 147A.
*Zonation location*.—Middle of the leaf.
*Zonation size*.—Medium.
*Petiole*.—Length: 3.5 cm to 4.5 cm. Diameter: 0.2 cm. Color: RHS 137B. Strength: Medium.
*Venation pattern*.—Palmate.
*Venation color*.—Upper surface: RHS 137B. Lower surface: RHS 138B.

Inflorescence:
*Lastingness of flowers on the plant*.—6 to 8 days.
*Umbels*.—Quantity of umbels per plant: 3 to 5. Length: 5.0 cm. Diameter: 8.5 cm.
*Individual florets of the umbel*.—Quantity of florets per umbel: 17 to 20. Depth: 1.5 cm. Diameter: 5.0 cm.
*Fragrance*.—Absent.

Flower buds:
*Cluster shape*.—Round.
*Cluster size*.—Length: 1.5 cm. Width: 1.7 cm.
*Surface texture*.—Pubescent, sparse.
*Bud*.—Height: 0.9 cm. Width: 0.6 cm. Shape: Round. Apex: Acute. Base: Obtuse. Margin: Entire. Color: RHS 144A.

Petals:
*Quantity per flower*.—5-8.
*Shape*.—Spatulate.
*Apex*.—Round.
*Base*.—Obtuse.
*Margin*.—Entire.
*Length*.—2.5 cm.
*Width*.—2.0 cm.
*Surface texture*.—Upper surface: Smooth. Lower surface: Smooth.
*Color of lobes*.—Upper lobes: Upper surface: Margin RHS 67A, large spot RHS 53A, base RHS 65B. Lower surface: RHS 67A basic, RHS 46B veins. Lower lobes: Upper surface: Margin RHS 67A, large spot RHS 53A, base RHS 65B. Lower surface: RHS 67A basic, RHS 46B veins.

Petaloids:
*Quantity per flower*.—1 to 2.
*Shape*.—Mixed-crippled, no further description possible.
*Apex*.—Round or acute.
*Base*.—Obtuse.
*Margin*.—Entire.
*Length*.—0.5 cm to 1.0 cm.
*Width*.—0.1 cm to 0.5 cm.
*Surface texture*.—Upper surface: Smooth. Lower surface: Smooth.
*Color*.—Upper surface: RHS 67A, RHS 53A. Lower surface: RHS 67A.

Sepals:
*Number per flower*.—5.
*Shape*.—Elliptic.
*Apex*.—Acute.
*Base*.—Obtuse.
*Margin*.—Entire.
*Surface texture*.—Upper surface: Smooth. Lower surface: Pubescent, sparse.
*Color*.—Upper surface: RHS 175A base, RHS 143A tip. Lower surface: RHS 175A base, RHS 143A tip.
*Length*.—1.1 cm.
*Width*.—0.4 cm.

Pedicel:
*Length*.—2.3 cm.
*Diameter*.—0.2 cm.
*Color*.—RHS 166A.
*Surface texture*.—Pubescent, sparse.
*Strength*.—Medium.

Peduncle:
*Length*.—6.0 cm.
*Diameter*.—0.4 cm.
*Color*.—RHS N199A.
*Texture*.—Pubescent, sparse.
*Strength*.—Strong.

Reproductive organs:
*Stamens*.—Quantity per flower: 8. Anther length: 0.3 cm. Filament length: 0.5 cm. Filament color: RHS 69D base, RHS 67A tip. Pollen amount: Moderate. Pollen color: RHS 166C.
*Pistils*.—Number: 1. Stigma color: RHS 53A. Style length: 0.2 cm. Style color: RHS 53A. Ovary arrangement: Central. Ovary color: RHS 146A base, RHS 53A top. Ovary diameter: 0.2 cm. Ovary length: 0.6 cm. Ovary texture: Pubescent, moderate.

Fruit and seed set: None observed.

Disease and pest/insect resistance: None observed.

COMPARISON WITH PARENTAL LINES AND KNOWN VARIETY

'KLEPZ21596' is distinguished from its parents as described in Table 1.

TABLE 1

| Comparison with Parental Lines | | | |
|---|---|---|---|
| Characteristic | 'KLEPZ21596' | Female parent | Male parent |
| Flower color | Purple-pink with a dark red spot and a light pink center | Cerise red with a light pink border and center | Cerise red with a light pink border and center |

'KLEPZ21596' can be compared to the commercial variety Toscana Dolce Vita Kiss Red Eye (patent status unknown). Differences between the two varieties are described in Table 2:

TABLE 2

| Comparison with Similar Variety | | |
|---|---|---|
| Characteristic | 'KLEPZ21596' | 'Toscana Dolce Vita Kiss Red Eye' |
| Flower color | Purple Pink, dark red spot, light pink center | Dark cerise red, light pink border and center |

We claim:

1. A new and distinct cultivar of *Pelargonium* Planted Named 'KLEPZ21596' as described and illustrated herein.

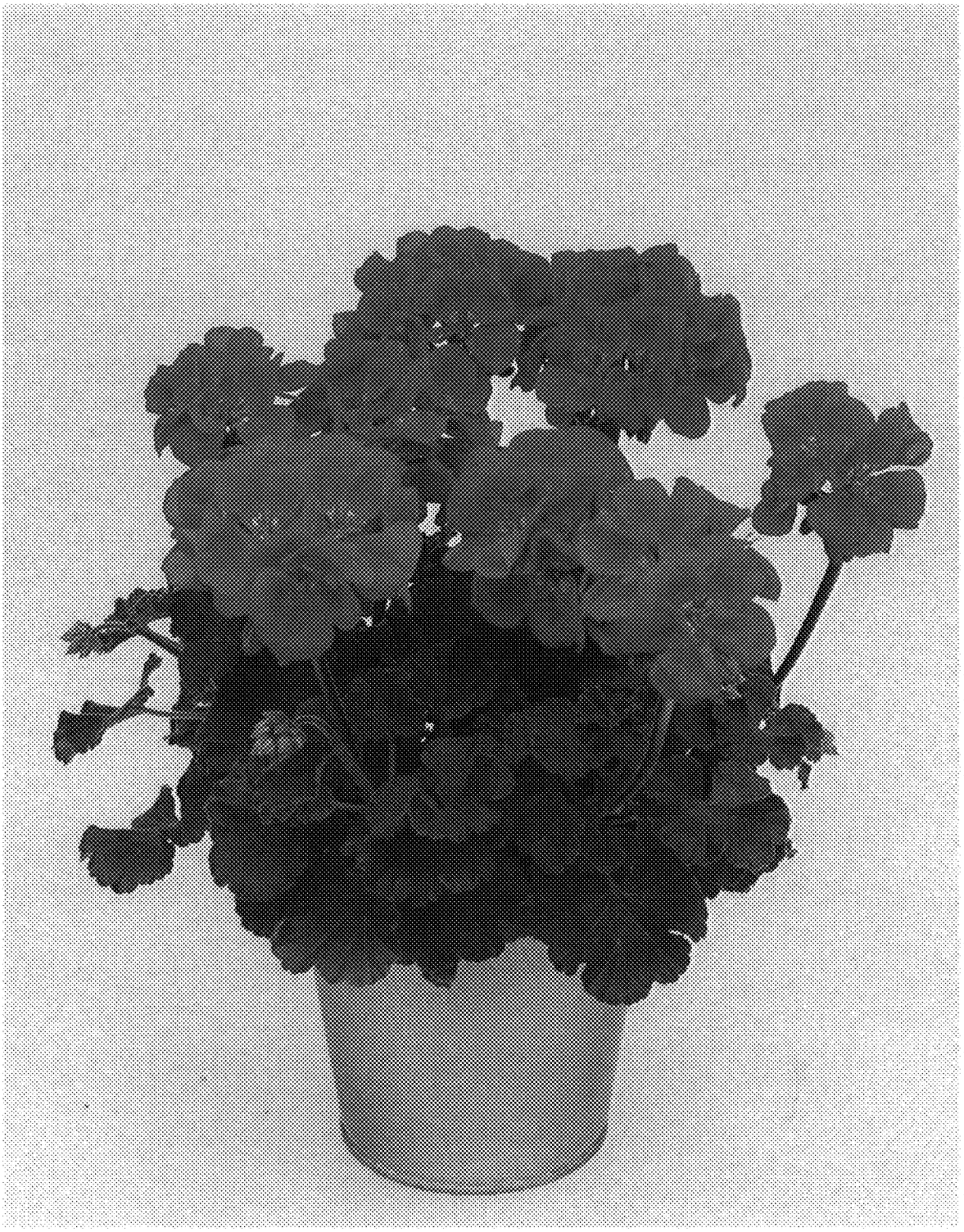

* * * * *